United States Patent [19]
Jensen et al.

[11] Patent Number: 5,592,693
[45] Date of Patent: Jan. 14, 1997

[54] AMPUTEE STUMP PROTECTOR CLOTHING

[76] Inventors: Darwin A. Jensen; Gwen R. Jensen, both of 135 S. 100 East, Centerfield, Utah 84622

[21] Appl. No.: 566,917

[22] Filed: Dec. 4, 1995

[51] Int. Cl.⁶ .............................. A41D 1/04; A41D 27/10
[52] U.S. Cl. ........................................ 2/115; 2/125; 2/270
[58] Field of Search ............................... 2/111, 115, 123, 2/125, 270, 114, 69, 122, 268, 104, 126, 90, 106, 113; 602/62, 63, 61; 623/36, 33; 128/846, 849, 873, 874, 878

[56] References Cited

U.S. PATENT DOCUMENTS

| | | | |
|---|---|---|---|
| 641,090 | 1/1900 | Elbaum | 2/122 |
| 1,264,971 | 5/1918 | Pickles | 2/69 |
| 1,296,966 | 3/1919 | Kaufman | 2/270 |
| 1,489,080 | 4/1924 | Lee | 2/122 |
| 1,926,194 | 9/1933 | Clark | 2/111 |
| 2,030,091 | 2/1936 | Behringer | 2/270 |
| 2,462,165 | 2/1949 | Condon | 2/111 |
| 2,497,262 | 2/1950 | Jacobson | 2/270 |
| 2,538,469 | 1/1951 | O'Brien | 128/874 |
| 2,677,130 | 5/1954 | O'Hayer | 2/270 |
| 2,828,738 | 4/1958 | Strelakos | 128/874 |
| 3,329,144 | 7/1967 | Liman | 2/59 |
| 3,561,009 | 2/1971 | Huggins | 2/90 |
| 3,600,717 | 8/1971 | McKeehan | 3/19 |
| 3,601,819 | 8/1971 | Herrmann | 3/1 |
| 3,744,054 | 7/1973 | Schultz | 2/16 |
| 4,479,272 | 10/1984 | Beldzisky | 3/16 |
| 4,664,946 | 2/1987 | Cremona-Bonato | 602/62 |
| 4,756,027 | 7/1988 | Buenos et al. | 2/123 |
| 4,781,720 | 11/1988 | Sherva-Parker | 623/16 |
| 4,923,474 | 5/1990 | Klasson et al. | 623/33 |
| 4,995,116 | 2/1991 | Beauchamp et al. | 2/69 |
| 5,033,127 | 7/1991 | Schmeltz | 2/269 |
| 5,108,455 | 4/1992 | Telikicherla | 623/33 |
| 5,117,507 | 6/1992 | Long | 2/158 |
| 5,208,920 | 5/1993 | Schaefer et al. | 2/269 |
| 5,258,037 | 11/1993 | Caspers | 623/36 |
| 5,326,351 | 7/1994 | Sarazin | 623/33 |

FOREIGN PATENT DOCUMENTS 558045  6/1958  Canada.

*Primary Examiner*—Amy B. Vanatta
*Attorney, Agent, or Firm*—Workman, Nydegger & Seeley

[57] ABSTRACT

A shirt worn by an amputee to protect the amputee against prosthesis friction and the friction caused by a prosthesis harness, the shirt having a closed distal portion corresponding to the amputee's amputation. When worn between an amputee's stump and a prosthesis, the shirt protects the amputee's stump against prosthesis friction and rubbing. A yoke or other padding can be added in the shoulder region of the shirt to further protect the amputee's shoulders against harness friction.

23 Claims, 8 Drawing Sheets

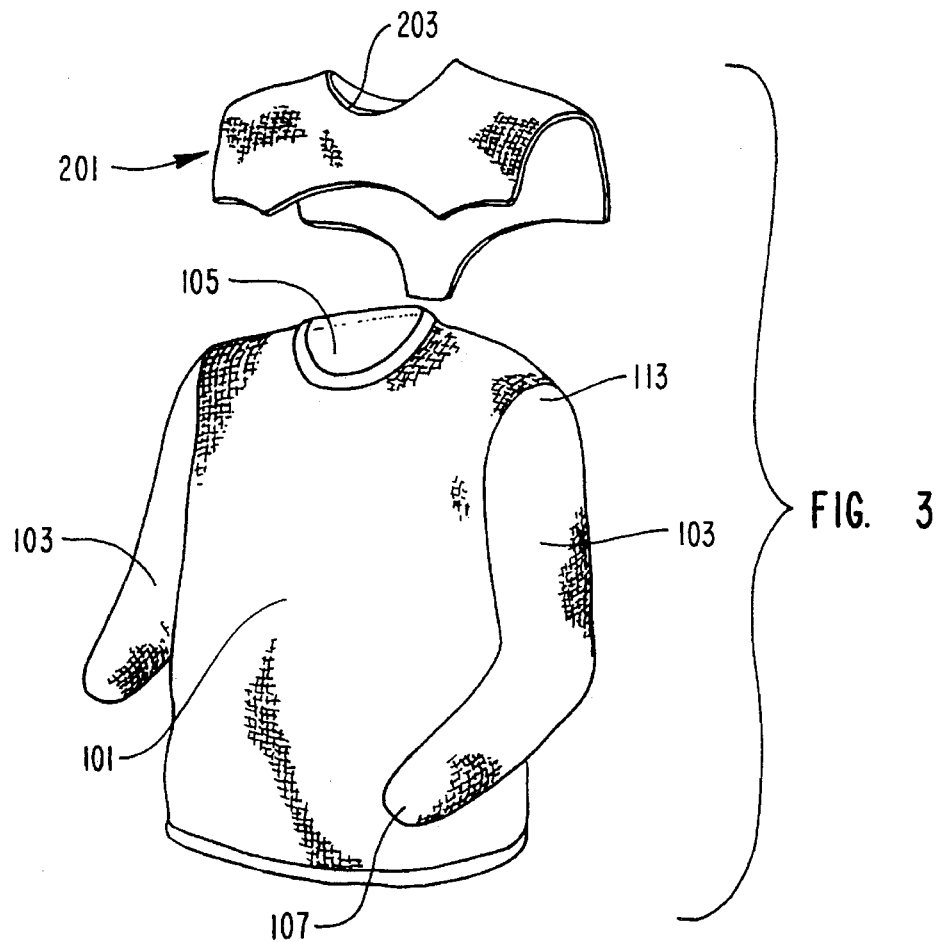
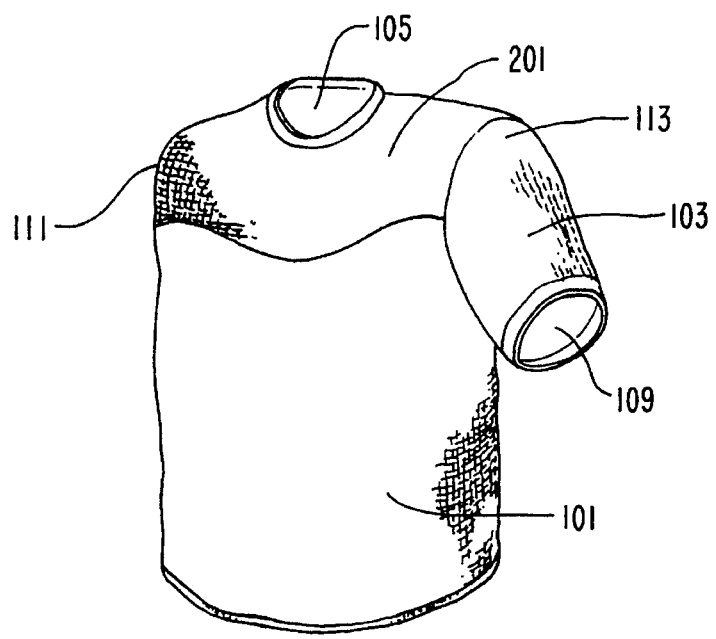

AMPUTEE STUMP PROTECTOR CLOTHING

BACKGROUND OF THE INVENTION

1. The Field of the Invention

This invention is in the field of amputee prosthetic liners and cushioning devices and discloses an amputee stump protector, designed in the form of clothing worn by the amputee, which protects an ampututation site from prosthesis friction and wear.

2. The Relevant Technology

One of the challenges faced by an amputee is to protect the fleshy end portion which forms on an amputation site against the rubbing and wear caused by the environment or, more particularly, by a prosthesis worn by the amputee. Friction against an amputee's stump may cause inflammation, scratching and bruising. Previously, stump socks or tube socks were used in an attempt to protect an amputee's stump against prosthesis friction and wear. A sock, for example, was placed over the stump, after which the prosthesis was placed on the sock-covered stump.

However, many problems were associated with employing stump socks or tube socks as prosthesis liners. For example, these devices continually roll down and congregate or bunch at the end of the stump in the cavity of the prosthesis socket. In addition, socks are often too tight on upper arms and are often too long to be used by the amputee. Furthermore, stump socks fail to protect the shoulder areas against friction caused by a prosthesis harness. It is also difficult for an amputee, particularly the dual arm amputee, to place such socks on the amputee's stump.

There has been a need in the art for a stump protector which is easy to use for the amputee, which covers the stump without the potential for bunching into the prosthesis socket, and which protects the stump and the shoulders against friction.

SUMMARY AND OBJECTS OF THE INVENTION

It is therefore an object of this invention to provide a stump protector which fits the amputee's stump.

It is another object of the invention to provide a stump protector which will not roll down or bunch up in the prosthesis socket.

It is another object of the invention to create a stump protector which is easy to put on for an amputee who may lack many of the skills normally used when putting on gloves, socks, or other clothing.

It is another object of the invention to provide a stump protector which is easy for the amputee to use, yet provides strong protection for the amputee.

It is another object of the invention to design such a stump protector which is preferably custom fit to the individual amputee, providing increased protection and decreasing the chance for rolling up into the prosthesis cavity.

It is another object of the present invention to provide a pad or friction decreasing material in the area where the amputee places a prosthesis harness.

It is a further object of the invention to provide technology which can be the basis for either single or double amputation protection devices and can be designed to fit any amputation site.

It is a further object of the invention to provide a stump protector which will not pinch or bind the stump or the portion of the limb neighboring the stump in order to retain the prosthesis in place.

It is a further object of the invention to provide a stump protector which is comfortable to wear, yet is also durable.

It is a further object of the invention to provide a stump protector which can incorporate a variety of textile styles and materials.

The applicant's invention is a shirt for protecting an amputee. The shirt has at least one closed distal portion corresponding to the amputee's amputation for protecting the amputee against friction and wear. When worn between an amputee's stump and a prosthesis, the shirt protects the amputee's stump against prosthesis friction and rubbing. A yolk or other padding can be added in the shoulder region of the shirt to further protect the amputee's shoulders against harness friction. The shirt is easy for the amputee to put on because the amputee can slide into the shirt, rather than pulling a stump protector up the amputees arm.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings in which:

FIG. 3 demonstrates the placement of a one-piece yoke onto a corresponding portion of the shoulders of the shirt.

FIG. 4 demonstrates that various kinds of shirts are possible, including a shirt having one sleeve with an open end and a closed shoulder on another side of the shoulder region.

FIGS. 5 through 9 demonstrate various designs for yokes.

FIGS. 5A through 9A demonstrate possible frontal portions of yokes while FIGS. 5A, through 9B demonstrate various rear portions of yokes, each of the yokes having a neck hole through the yoke. The front pieces in FIGS. 5A through 9A correspond to the back pieces in FIG. 5B through 9B, respectively.

DETAILED DESCRIPTION OF THE PREFERRED EMBODIMENTS

Figure 1:
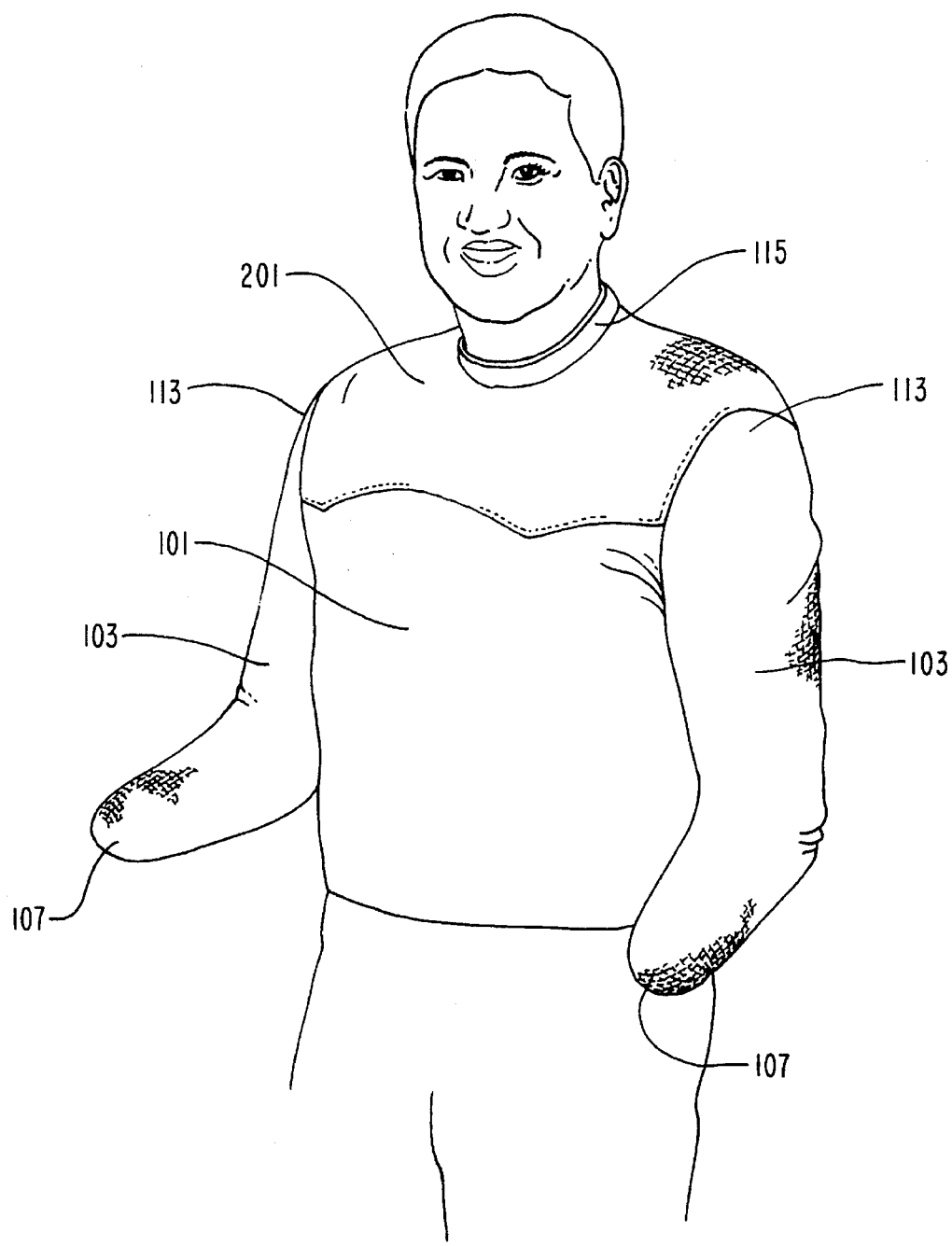
FIG. 1 is a perspective view of the invention demonstrating the preferred shirt having a yoke and demonstrating two sleeves, each sleeve having closed distal ends.

As shown in FIGS. 1–4, a shirt is herein disclosed having a body 101, which preferably has a tubular shape. The shirt further has a shoulder region, the shoulder region having a neck opening 105. The shirt includes at least one closed distal portion corresponding to the amputee's amputation, such as a closed shoulder 111, or a sleeve 103 having a proximal end 113 connected to the body 101 for receiving an arm therethrough and a closed distal end 107 for protecting the distal portion of the arm.

As used throughout this application and claims, the term "amputation" or "amputated arm" refers to any portion of the arm or hand which has suffered an amputation including the entire arm or hand. The shirt may thus be used to protect amputees who have suffered either a complete or a partial amputation of the arm or hand.

Turning to FIG. 1, the closed distal end 107 of a sleeve 103 may have a rounded shape, a U-shape, a conical shape, a frustoconical shape, or another shape which best encapsulates the stump of an amputated member. In a preferred embodiment, the shirt is designed to custom fit the stump of at least one amputated arm or hand retaining the distal end 107 of the sleeve 103 snugly against the stump, thereby protecting the stump from injury or friction caused by a prosthesis 301 worn over the stump, as shown in FIG. 2.

Figure 2:
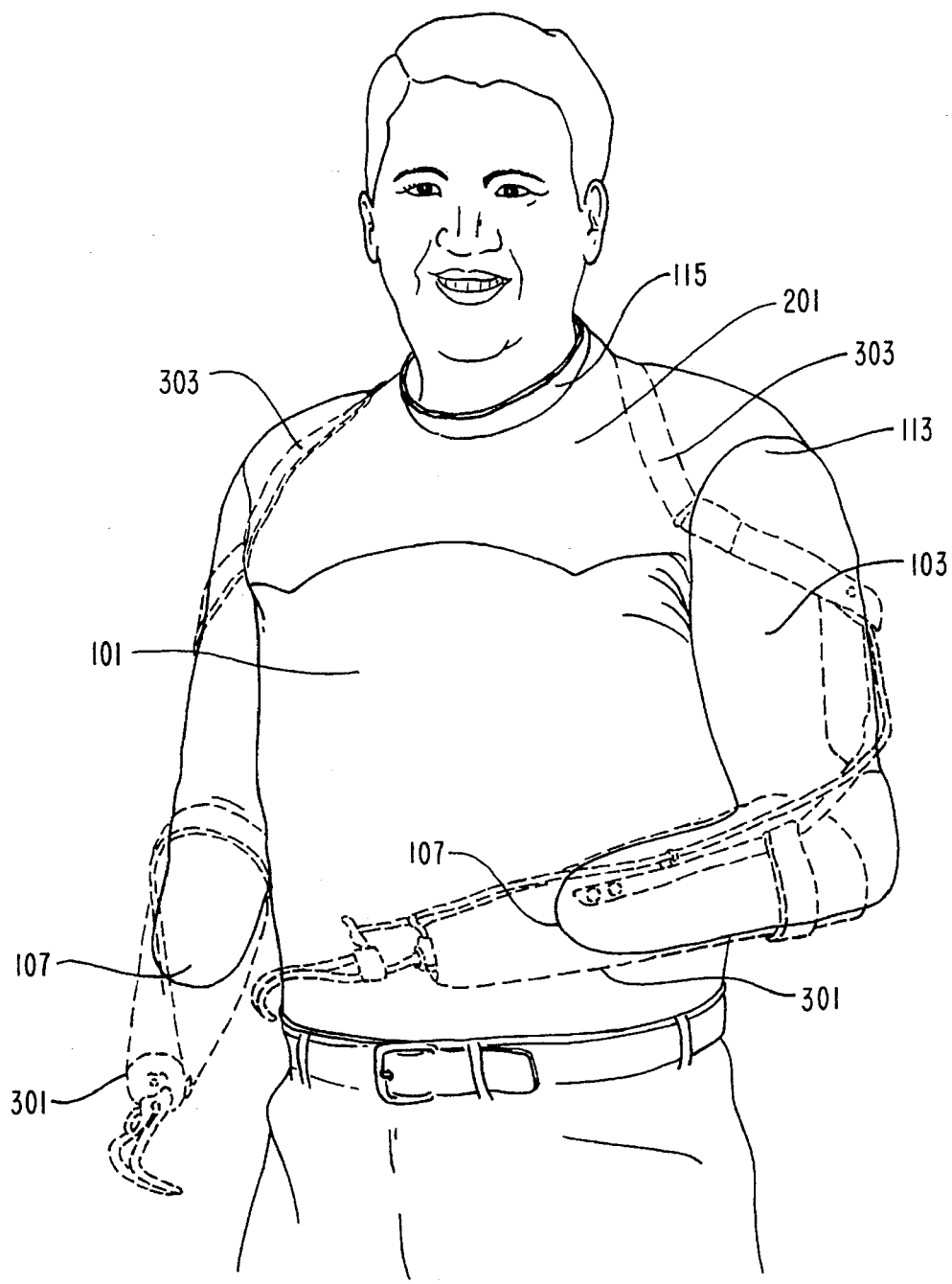
FIG. 2 is a perspective view of the invention worn under a prosthesis, the harness of the prosthesis typically fitting around the arm and over the shoulder onto the yoke portion of the shirt.
Figure 5A:
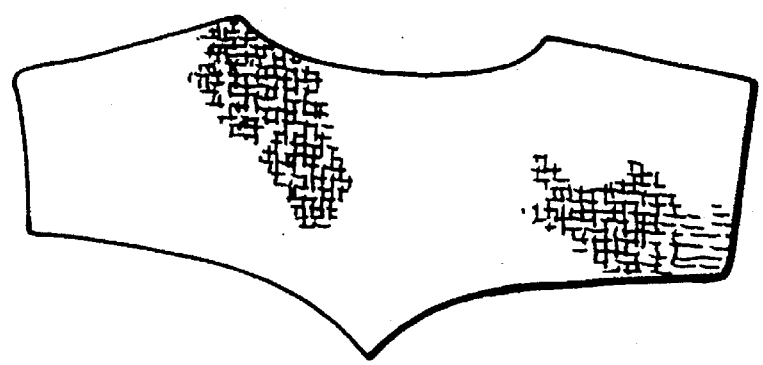
Figure 5B:
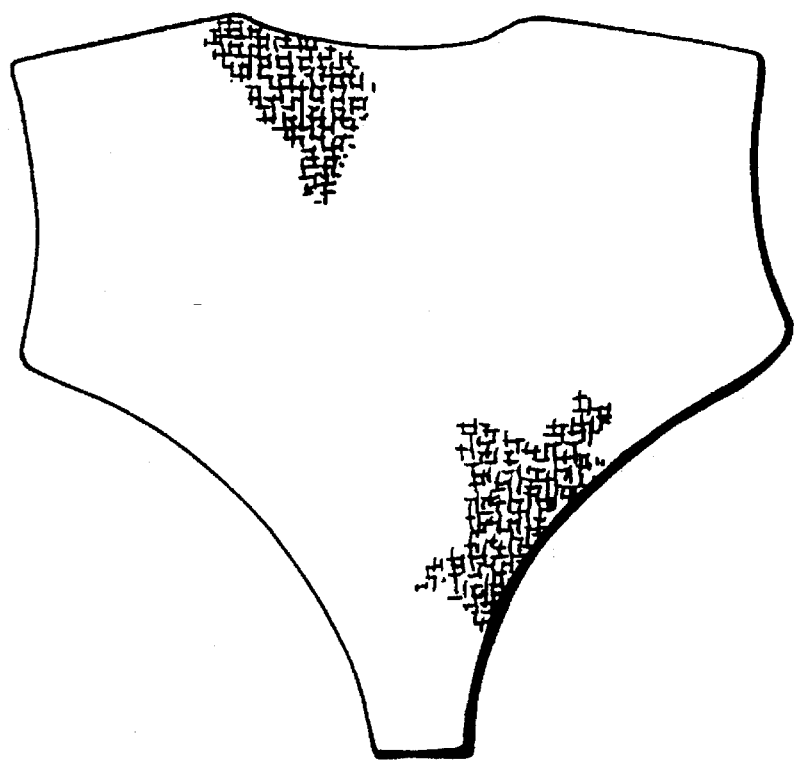
Figure 6A:
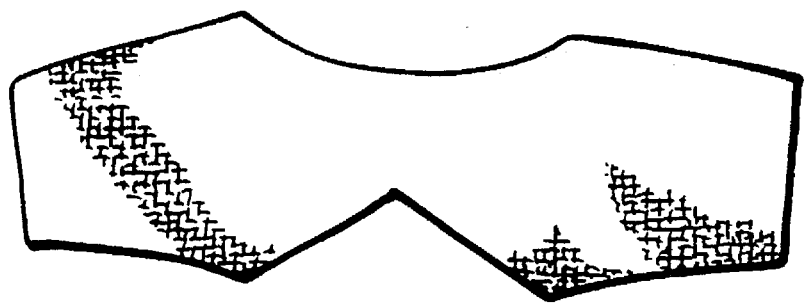
Figure 6B:
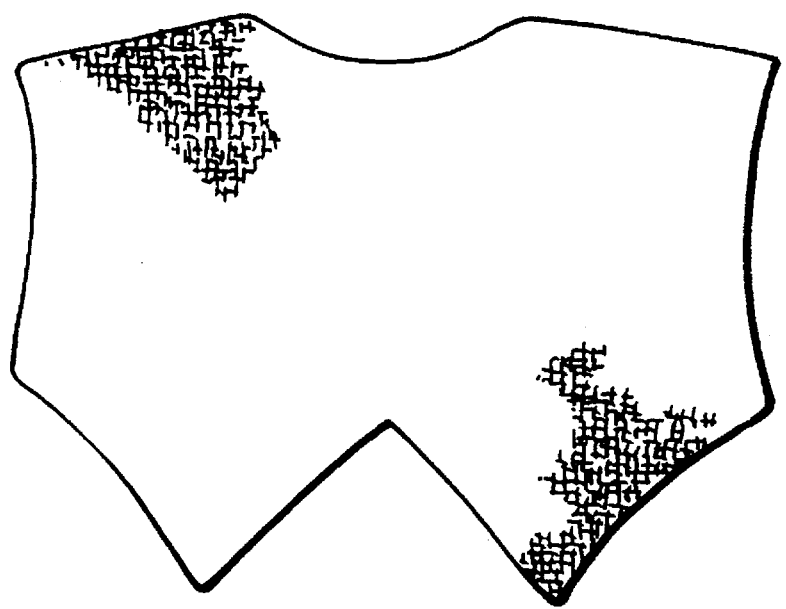
Figure 7A:
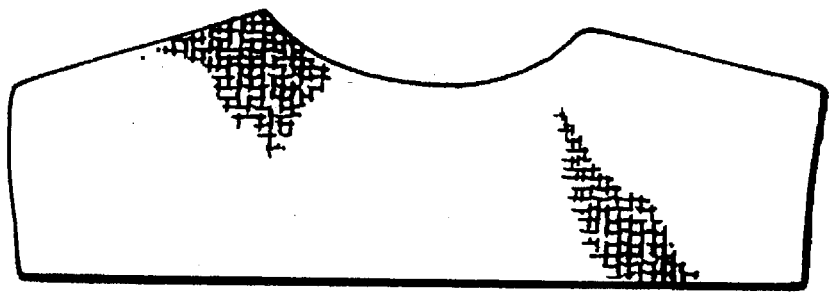
Figure 7B:
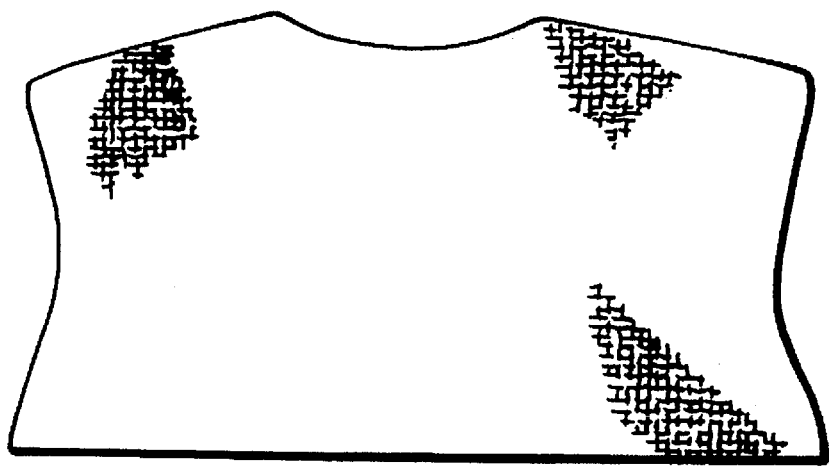
Figure 8A:
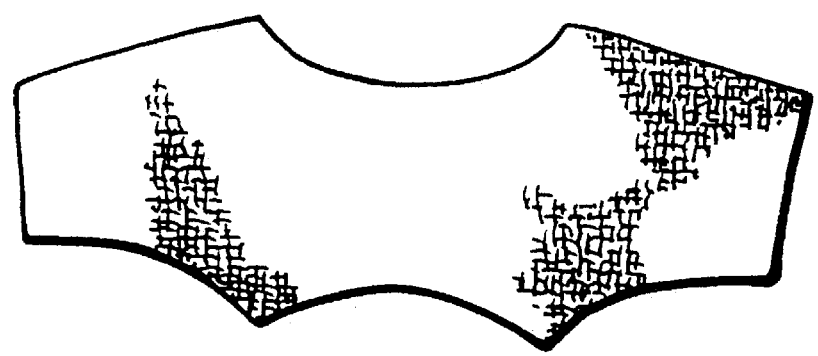
Figure 8B:
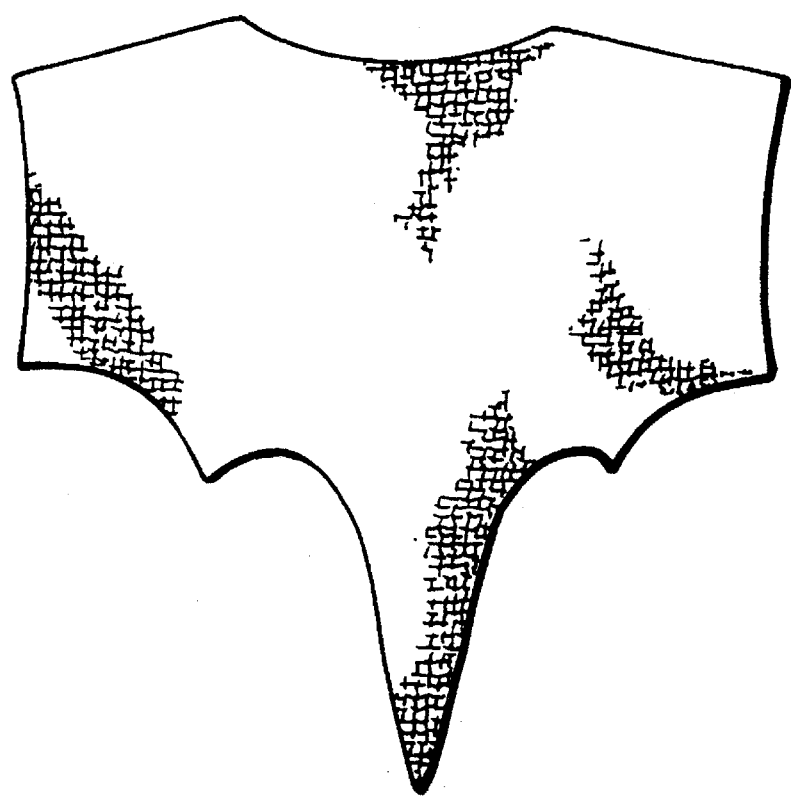
Figure 9A:
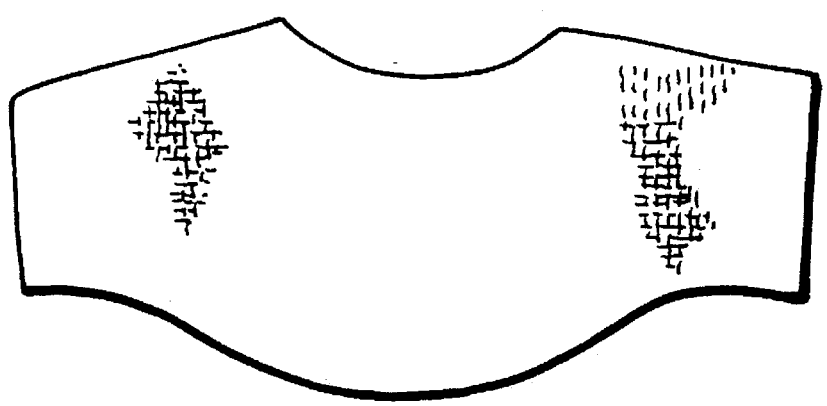
Figure 9B:
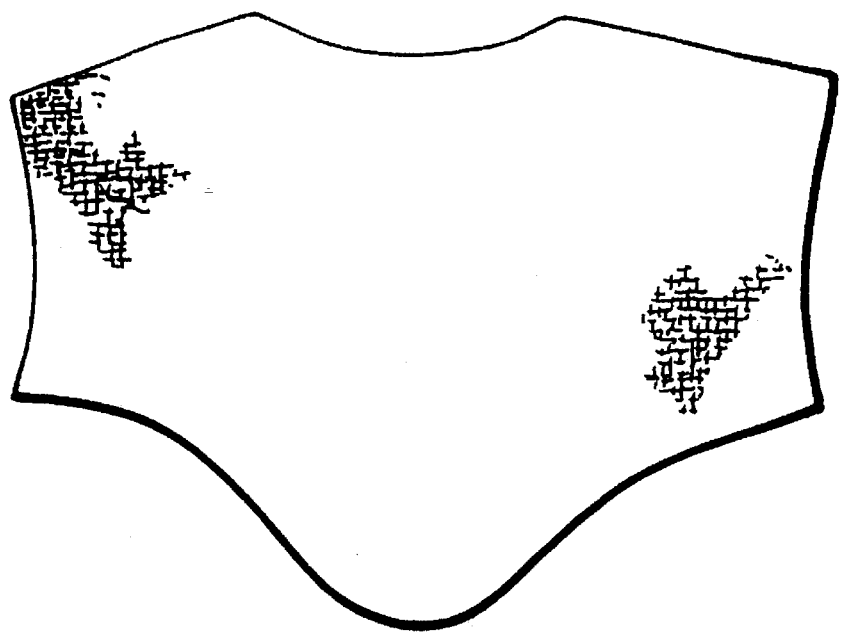

As shown in FIGS. 1–3, in a preferred embodiment of the shirt, a yoke 201 overlays the shoulder region of the shirt, forming a double layer in the shoulder region. The yoke 201 may be made of the same material or of a different material as the shirt and may be thicker, the same thickness, or thinner than the shirt. Padding may exist between the shirt and the yoke 201 or the yolk 201 may be a thick padded area. The padding and/or the double layer creates a cushion for the prosthesis harness 303, which can often rub and thereby create discomfort in the shoulder area. Foam or other insulated material is contemplated for padding on, or around, or under the yoke 201.

The double layer provides for slidable cushioning in that it allows for rubbing of the yoke 201 against the shoulder region of the shirt when the harness 303 rubs on the yoke 201, as opposed to rubbing of a single layer against a person's shoulders.

As demonstrated in FIG. 3, the yoke comprises a neck opening 203 corresponding preferably to the neck opening 105 of the shirt. Possible corresponding front and back yolk designs are enclosed in FIGS. 5 through 9.

A second sleeve may exist on the shirt, the sleeve having an open proximal end 113 connected to the body 101 for receiving a second arm therethrough and a closed distal end 107 for protecting the distal portion of the second arm, as shown in FIG. 1, or an open distal end 109 for a non-amputated arm, as shown in FIG. 4.

Preferably the sleeve 103 tapers from the proximal end 113 of the sleeve 103 to the distal end 107 of the sleeve 103 and fits tighter than most commercially produced shirts. Tight fitting is important to avoid entanglement with the action of the prosthesis harness 303.

While a design featuring buttons down the front is possible, a closed front style has proven most effective in light of the harness 303 pulling which may occur on the front of the shirt.

Turning to FIG. 4, it is possible for the shirt to have a closed shoulder 111 for use by an amputee who has lost an entire arm. In addition to the closed shoulder 111, the shirt having a closed shoulder 111 may comprise an open-ended sleeve 109, or a sleeve having a closed distal end 107 as shown in FIGS. 1–3. The closed shouldered shirt corresponds to and protects the amputee's amputation by covering the amputated area.

The shirt and/or yoke material may be selected from a wide variety of clothing material known in the art, including cotton, fleece, linen, wool, synthetic, terry cloth, jersey, HEALTHTEX, a combination of cotton and polyester, polyester, knit, or combinations of the foregoing. The preferred material for both the yoke 201 and the shirt is a cotton/polyester blend, such as a 50/50 cotton/polyester knit blend which provides the maximum capability of long wear and comfort in light of the rubbing which occurs by a prosthesis against the closed distal end of the shirt and by the harness.

While it is possible to wear the disclosed shirt without wearing the prosthesis, in order to protect the amputee's stump from the environment, the protection provided by the invention is particularly useful in that it reduces injury and discomfort resulting from the friction between a prosthesis and the stump of an amputated limb. This friction may cause rubbing, inflammation, wear, scratching, or bruising.

It is contemplated that the shirt could be an outer garment or could be an undergarment, either embodiment providing epidermal protection for the fleshy end portion of the amputation site.

The disclosed shirt is, in many instances, easier for the amputee to put on than a mere stump sock, which requires the ability to pull the sock up one's arm. In the present invention, it is possible to put on the shirt merely by sliding into the shirt—a much easier movement, particularly for the dual arm amputee.

A variety of methods exist for making the shirt that is disclosed and claimed. One method for making the shirt comprises cutting out an appropriate stock material in the shape of the body 101, including a shoulder region, stitching the material together to form the body, and closing a distal portion of the shirt corresponding to the amputee's amputation, thereby protecting the amputee. Additional steps are added in the preferred embodiment, including mounting a yolk in the shoulder region.

The material is preferably initially cut out into front and back body portions and front and back yoke portions. Preferably, the front yoke piece is then sewn onto the front body piece and the back yoke piece is sewn onto the back body piece with a single needle.

A corresponding front and back shoulder portion may be surged together, after which a neck band 115 is surged on, following which the other front and back shoulder portions are surged together. Alternatively, both shoulders may be surged together, after which the neck band is surged in. Preferably, the shoulder seams and at least a portion of the neck band seam, such as the back portion of the neck band 115 seam, are then coverstitched to cushion wear from these seams, which underlie the prosthesis harness 303, against the shoulders and neck of the amputee.

Preferably at this point, one or two sleeves are then surged in, after which a distal end of one or both of the sleeves is closed, following which the sides of the body and possibly, a distal end in the shoulder region (for a closed shoulder as in FIG. 4), are surged. It is possible to cover stitch the area encapsulating or surrounding the stump or amputee site. Preferably, the bottom of the body is then hemmed, as is the distal portion of an open-ended a sleeve, if applicable. The remaining threads are then preferably clipped, right side out.

In light of the purpose of protecting an amputee's stump against various kinds of friction and wear, it is desirable to minimize the number and size of seams wherever possible. It is also preferred to place the seam of a sleeve protecting an amputated limb on the bottom of the sleeve, as opposed to the top, to minimize contact with the top side of the arm. It is also preferred when coloring the shirt to use dyes which do not cause irritation to the wearer's skin. Certain commonly used black and red dyes may cause skin irritation, while commonly used white, tan and blue dyes may create less irritation to the wearer.

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A shirt for protecting an amputee having at least one amputated arm having a stump, the shirt comprising:
    a body having a shoulder region; and
    at least one sleeve including:
        a proximal end connected to the body and having an opening in the shoulder region for receiving the at least one amputated arm therethrough; and
        a closed distal end that extends integrally from the sleeve such that it is permanently closed and tapered to closely encapsulate the stump of the at least one amputated arm.

2. A shirt as defined in claim 1, wherein the sleeve tapers from the proximal end to the distal end.

3. A shirt as defined in claim 1, wherein the distal end of the sleeve has a U shape.

4. A shirt as defined in claim 1, wherein the distal end of the sleeve has a conical shape.

5. A shirt as defined in claim 1, wherein the distal end of the sleeve has a rounded shape.

6. A shirt as defined in claim 1, wherein the shirt is designed to custom fit the at least one amputated arm and a stump of the at least one amputated arm, retaining the closed distal end of the sleeve snugly against the stump and retaining the sleeve snugly against the at least one amputated arm.

7. A shirt as defined in claim 1, further comprising a yoke overlaying the shoulder region of the shirt, thereby creating a plurality of layers in the shoulder region of the shirt.

8. A shirt as defined in claim 1, wherein padding exists in the shoulder region of the shirt.

9. A shirt as defined in claim 1, further comprising a yoke overlaying the shoulder region of the shirt, thereby creating a plurality of layers in the shoulder region of the shirt, and wherein padding exists between the yoke and the shoulder region of the shirt.

10. A shirt as defined in claim 1, wherein the shirt comprises shoulder seams, a neck band, and a neck band seam, and wherein the shoulder seams and at least a portion of the neck band seam are cover-stitched to cushion the seams.

11. A shirt as defined in claim 1, further comprising a second sleeve having:
    a proximal end connected to the body and having an opening in the shoulder region for receiving a second amputated arm therethrough; and
    a closed distal end that extends integrally from the sleeve such that it is permanently closed and tapered to closely encapsulate a stump of the second amputated arm.

12. A shirt as defined in claim 1, further comprising:
    a second sleeve having an open proximal end connected to the body for receiving a second arm therethrough.

13. A shirt as defined in claim 1, wherein the shirt is made from a material selected from the group consisting of cotton, fleece, linen, wool, polyester, jersey, terry cloth, and cotton/polyester blend.

14. A shirt for protecting an amputee having at least one amputated arm having a stump against friction caused by a prosthesis and its associated harness, the shirt comprising:
    a substantially tubular body having a shoulder region;
    a yoke overlaying the shoulder region such that the yoke and shoulder region form a plurality of layers for slidably cushioning the amputee's shoulders against harness friction; and
    at least one sleeve including:
        a proximal end connected to the body of the shirt and having an opening in the shoulder region for receiving the at least one amputated arm therethrough; and
        a closed distal end that extends integrally from the sleeve for snug placement over the stump of the at least one amputated arm such that the closed distal end of the sleeve is permanently closed and tapered such that it closely encapsulates the stump and such that when the shirt is worn under a prosthesis the closed distal end of the shirt protects the stump against prosthesis friction.

15. A shirt as defined in claim 14, wherein the sleeve tapers from the proximal end to the distal end.

16. A shirt as defined in claim 14, wherein the shirt comprises shoulder seams, a neck band, and a neck band seam, and wherein the shoulder seams and at least a portion of the neck band seam are cover-stitched to cushion the seams.

17. A shirt as defined in claim 14, wherein the shirt is made from a material selected from the group consisting of cotton, fleece, linen, wool, polyester, jersey, terry cloth, and cotton/polyester blend.

18. A shirt for protecting an amputee having at least one completely amputated arm, the shirt comprising:
    a body having a shoulder region; and
    at least one side in the shoulder region corresponding to the completely amputated arm that is sleeveless and permanently closed such that the shirt completely and closely covers and encapsulates the shoulder region corresponding to the completely amputated arm.

19. A shirt as defined in claim 18, further comprising a yoke overlaying the shoulder region of the shirt, thereby creating a plurality of layers in the shoulder region of the shirt.

20. A method for manufacturing a shirt for protecting an amputee having at least one amputated arm having a stump, the method comprising:
    manufacturing a body of the shirt having a shoulder region; and
    attaching at least one sleeve to the shoulder region of the body, the at least one sleeve including:
        a proximal end connected to the body and having an opening in the shoulder region for receiving the at least one amputated arm therethrough; and
        a distal end that extends integrally from the sleeve such that it is permanently closed and tapered to closely encapsulate the stump of the at least one amputated arm.

21. A method as defined in claim 20, wherein the attaching step comprises attaching the proximal end of the at least one sleeve to the shoulder region of the body of the shirt and thereafter closing the distal end of the at least one sleeve in order to thereby permanently close the distal end of the at least one sleeve.

22. A method as defined in claim 21, further comprising the step of mounting a yoke within the shoulder region such that the yoke and shoulder region form a plurality of layers for slidably cushioning the amputee's shoulders against harness friction.

23. A method as defined in claim 22, wherein the shoulder region includes shoulder seams, the method further comprising:

attaching a neck band having a neck band seam; and cover-stitching the shoulder seams and at least a portion of the neck band seam to cushion the seams.

* * * * *

UNITED STATES PATENT AND TRADEMARK OFFICE
CERTIFICATE OF CORRECTION

PATENT NO. : 5,592,693
DATED : January 14, 1997
INVENTOR(S) : Darwin A. Jensen and Gwen R. Jensen It is certified that error appears in the above-indentified patent and that said Letters Patent is hereby corrected as shown below:

At col. 1, line 37, before "shoulders" delete ".".

At col. 3, line 26, after "or the" change "yolk" to --yoke--.

At col. 3, line 40, after "back" change "yolk" to --yoke--.

At col. 4, line 34, before "in the" change "yolk" to --yoke--.

At col. 4, line 56, after "stump or" change "amputee" to --amputation--.

Signed and Sealed this

First Day of April, 1997

*Attest:*

BRUCE LEHMAN

*Attesting Officer*     *Commissioner of Patents and Trademarks*